United States Patent [19]

Wilson et al.

[11] Patent Number: 5,693,537
[45] Date of Patent: Dec. 2, 1997

[54] COMPARTMENTALIZED TISSUE CULTURE FLASK

[76] Inventors: John R. Wilson, 173 Windsor La., New Brighton, Minn. 55112; Martin L. Wolf, 1280 Keston St., St. Paul, Minn. 55108

[21] Appl. No.: 324,563

[22] Filed: Oct. 18, 1994

Related U.S. Application Data

[63] Continuation-in-part of Ser. No. 268,073, Jun. 28, 1994, abandoned.

[51] Int. Cl.⁶ ................................. C12N 5/00; C12M 3/06
[52] U.S. Cl. .................. 435/401; 435/297.5; 435/304.2; 435/304.3
[58] Field of Search ................. 435/240.1, 240.2, 435/240.23, 240.241, 240.25, 284–286, 296–301, 311, 313, 809, 286.6, 288.1–288.5, 297.1, 297.2, 297.5, 304.1, 304.2, 304.3, 305.1–305.4, 399, 401, 402

[56] References Cited

U.S. PATENT DOCUMENTS

| | | | |
|---|---|---|---|
| 4,296,205 | 10/1981 | Verma | 435/285 |
| 4,661,455 | 4/1987 | Hubbard | 435/285 |
| 4,748,124 | 5/1988 | Vogler | 435/285 |
| 4,839,292 | 6/1989 | Cremonese | 435/311 |
| 4,937,196 | 6/1990 | Wrasidlo et al. | 435/284 |
| 5,068,195 | 11/1991 | Howell et al. | 435/284 |
| 5,153,131 | 10/1992 | Wolf et al. | 435/284 |
| 5,225,346 | 7/1993 | Matsumiya et al. | 435/284 |

FOREIGN PATENT DOCUMENTS

0155237   9/1985   European Pat. Off. .

OTHER PUBLICATIONS

GIBCO BRL Catalogue & Reference Guide (1992) pp. 7–9 and 78.

*Primary Examiner*—William H. Beisner
*Attorney, Agent, or Firm*—Sprung Kramer Schaefer & Briscoe

[57] ABSTRACT

A cell culture device comprising a container having a cell culture compartment defined by a lower gas permeable film and an upper sheet selectively permeable to compounds of selected sizes. The device is adapted to allow culture medium to reside between the upper sheet and the lower gas permeable film. A basal medium compartment is located above the upper sheet and is adapted to allow basal medium to reside upon the upper sheet. Each compartment contains an access port. A gas film support below and in partial contact with the gas permeable film holds the gas permeable film in a substantially horizontal position so that suspension or adherent cells can distribute across the surface of the gas permeable film.

24 Claims, 6 Drawing Sheets

COMPARTMENTALIZED TISSUE CULTURE FLASK

This is a continuation-in-part of application Ser. No. 08/268,073, filed Jun. 28, 1994, now abandoned.

BACKGROUND

1. Field of the Invention

This invention relates to a device and a method for growing cells or tissue in vitro.

2. Description of Prior Art

In vitro growth of mammalian cells is commonly conducted in static culture vessels such as tissue culture flasks and spinner flasks. In this type of culture, a portion of the cell culture medium is periodically removed and replaced as cells consume nutrients and produce waste products. This protocol leads to limited cell density, limited cell secreted product concentration, and periodic shifts in nutrient concentration.

Marbrook used a dialysis membrane to separate cells and cell secreted products from the basal medium (Marbrook, J., "Primary Immune Response in Cultures of Spleen Cells", the Lancet, 2, 1279–1281 [1967]). In this device, an inner concentric chamber resides within an outer concentric chamber. The bottom of the inner chamber is comprised of a dialysis membrane which is submerged in basal medium contained in the outer chamber. Cells reside on the membrane receiving nutrients and delivering waste products. Continuous dialysis becomes limited as the membrane loses substrate transport capacity due to the cell mass that resides upon it. Thus, the ability to carry out long term culture is compromised.

Verma (U.S. Pat. No. 4,296,205 issued Oct. 20, 1981) teaches of the use of a tissue culture shelf placed in the cell culture compartment to keep cells from directly contacting and clogging the dialysis membrane. The tissue culture shelf has perforations to allow movement of nutrients to the cells. During the culture of suspension cells, the cells and cellular debris are capable of moving through the perforations and coming to rest upon the dialysis membrane, limiting continuous dialysis in long term culture. Also, the architectural structure of the shelf can lead to microenvironments as concentration gradients are unevenly distributed across the surface of the plate.

Vogler (U.S. Pat. No. 4,748,124 issued May 31, 1988) describes a cell culture compartment that is defined by a lower gas permeable, liquid impermeable sheet and an upper dialysis membrane. This configuration keeps the dialysis membrane from clogging as cells do not reside upon it, yet dialysis can become limited by other means. Also, the ability to vary oxygen tension is limited relative to Marbrook and Verma. Furthermore, the surface chemistry of materials used to allow gas transfer are limited and in some cases can be undesirable for protein or cell contact. Finally, the teaching does not lead to high density cell culture relative to traditional static culture methods.

The architecture of Vogler can allow dialysis of the cell compartment to become limited. A major problem can arise as liquid evaporates from the growth chamber. Vapor transmission across gas permeable surfaces can be substantial and the loss of liquid will lead to termination of dialysis as liquid contact with the dialysis membrane ceases. Loss of dialysis will also result from off gassing of cell culture medium. Cell culture medium is typically stored at 4 degrees Celsius. As the medium rises in temperature, the gas carrying capacity is reduced and gas bubbles rise and come in contact with the dialysis membrane.

The gas permeable, liquid impermeable sheet of the cell culture compartment limits options available for controlling pericellular pH and $P_{O2}$. In the prior configurations of Marbrook and Verma, the oxygen tension could be varied by adjusting the liquid level of the cell culture compartment. The structure and method taught by Vogler require oxygen tension be varied by altering the ambient conditions of the atmosphere surrounding the device.

Oxygen tension is very important to cell viability and protein secretion (Reuveny et at., "Factors Affecting Cell Growth and Monoclonal Antibody Production in Stirred Reactors", Journal of Immunological Methods, 86, 53–59 [1986]). The gas permeability of commercially available liquid impermeable sheets and the impact upon pericellular pH and $P_{O2}$ is described in detail by Jenson et at. (Jenson M. D., Wallach D. F. H., and Sherwood P., "Diffusion in Tissue Cultures on Gas-permeable and Impermeable Supports", J. Theor. Biol. (1976) 56, 443–458). The oxygen demands of various cell types combined with the gas permeability of various gas permeable, liquid impermeable sheets will dictate a specific steady state pericellular pH and $P_{O2}$ for each combination. This means cell lines are subject to very limited pericellular conditions. Creating different pericellular conditions is achieved by altering the ambient conditions of the incubator in which the device resides. As a practical matter, this is difficult for researchers who maintain incubators at standard conditions for a wide variety of simultaneous uses.

Gas permeable, liquid impermeable sheets also limit the surface chemistry available for support of cells and protein structures. The proliferation and function of many cell types is strongly affected by the chemical nature of the surfaces they reside upon. The surface chemistry of liquid impermeable material is incompatible with many cell types and protein structures. Also, hydrophobic material which is often the basis for gas permeable, liquid impermeable films, can cause non-specific protein binding. This in turn can lead to depletion of soluble growth factors. Thus, further modification to the materials may be required for optimization of the cell environment.

The architecture of Vogler also leads to limited cell density. The growth chamber will deform in shape due to the weight of liquid residing upon it and pressure of fluid expansion, leading to a sagging gas permeable sheet. This allows suspension cells to settle in the low point of the sheet. High localized cell densities at the low point of the sheet leads to excessive resistance to flux of nutrients and a localized reduction in cell viability. Furthermore, the cells are unable to expand to other areas of the gas permeable sheet.

It is accordingly an object of the present invention to provide a method and device for the long term culture of anchorage dependent cells and suspension cells at high density, simultaneously allowing variable oxygen tension, an even distribution of cells across the bottom of the culture compartment, uninterrupted dialysis, and a wide variety of surface chemistry options. Still further objects and advantages will become apparent from consideration of the ensuing description and drawings.

SUMMARY OF THE INVENTION

Many of the problems of the prior art are solved by a compartmentalized cell culture flask constructed in accordance with this invention to allow cells to be cultured at high density over a long period of time.

According to one embodiment of the invention, two compartments reside one above the other and are in communication with one another by a membrane selectively permeable to a specific class of molecules. The upper compartment houses basal medium and the lower compartment houses cells and cell culture medium. Selected nutrients and waste products are permitted to move freely between the basal medium and the cell culture medium.

The lower cell culture compartment is configured such that it's bottom is comprised of a lower gas permeable film that is constrained in a horizontal and flat position. In this manner, suspension and adherent cells can spread out evenly across the entire surface. The gas permeable film can be any biocompatible liquid permeable or impermeable, hydrophobic or hydrophilic, porous or non porous material which provides the appropriate pericellular environment and surface chemistry for a specific cell culture application.

The upper basal medium compartment and the lower cell culture compartment are configured to allow pipette access and prevent pressurization due to temperature increase. The cell culture compartment is configured to prevent loss of dialysis due to evaporation or off-gassing, compensate for liquid flux from the basal medium reservoir, and allow high cell density cultures to be maintained over a long period of time.

According to a second embodiment of the invention, evaporative loss of cell culture medium can be controlled independent of ambient conditions by providing gaseous exchange of the cell culture compartment by way of the humidified gas of the upper basal medium compartment.

According to a third embodiment of the invention, oxygen tension within the cell culture compartment can be accurately controlled independent of ambient conditions by adding a third compartment that utilizes a variable level of liquid to alter oxygen tension.

According to a third embodiment of the invention, the cell culture compartment volume can be varied during operation with out interrupting dialysis.

With these structures, a method of culturing cells at high density becomes available. Also, a method of controlling oxygen tension surrounding cells becomes available by utilizing a liquid barrier to oxygen flux.

With the invention so stated, many of the problems associated with the prior art are solved. Long term high density in vitro culture of both suspension and adherent cells is possible with simultaneous provisions for variable oxygen tension, controlled evaporation, long term maintenance of small cell compartment liquid volumes, and uninterrupted dialysis.

REFERENCE NUMERALS IN DRAWINGS 10 compartmentalized tissue culture flask
20 membrane
30 basal medium compartment
40 cell culture compartment
50 culture medium
60 basal medium
70 cell culture compartment access port
80 cell culture compartment access port cap
90 basal medium access port
100 basal medium access port cap
110 membrane support
120 gas permeable film
130 gas film support
140 gas access opening
150 feet
170 basal medium head space
180 culture medium head space
190 gas access channel
200 gas access channel cover
210 drain port
220 variable oxygen control compartment
230 lower gas permeable film
240 oxygen control compartment bottom
250 oxygen control compartment access port
260 liquid resistor
270 upper membrane support

DETAILED DESCRIPTION

Figure 1:
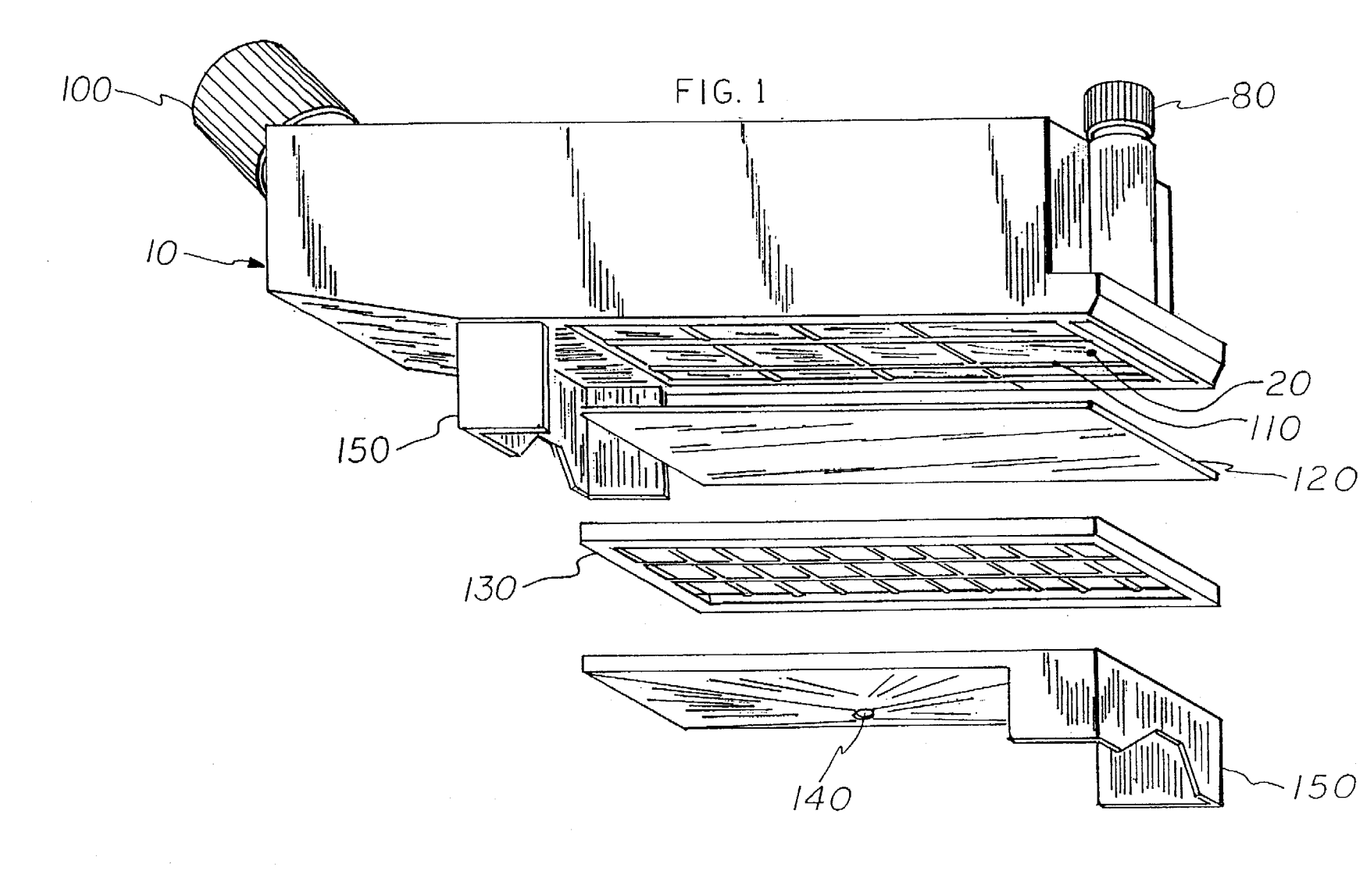
FIG. 1 is an exploded view of a compartmentalized tissue culture flask in accordance with the present invention.
Figure 2:
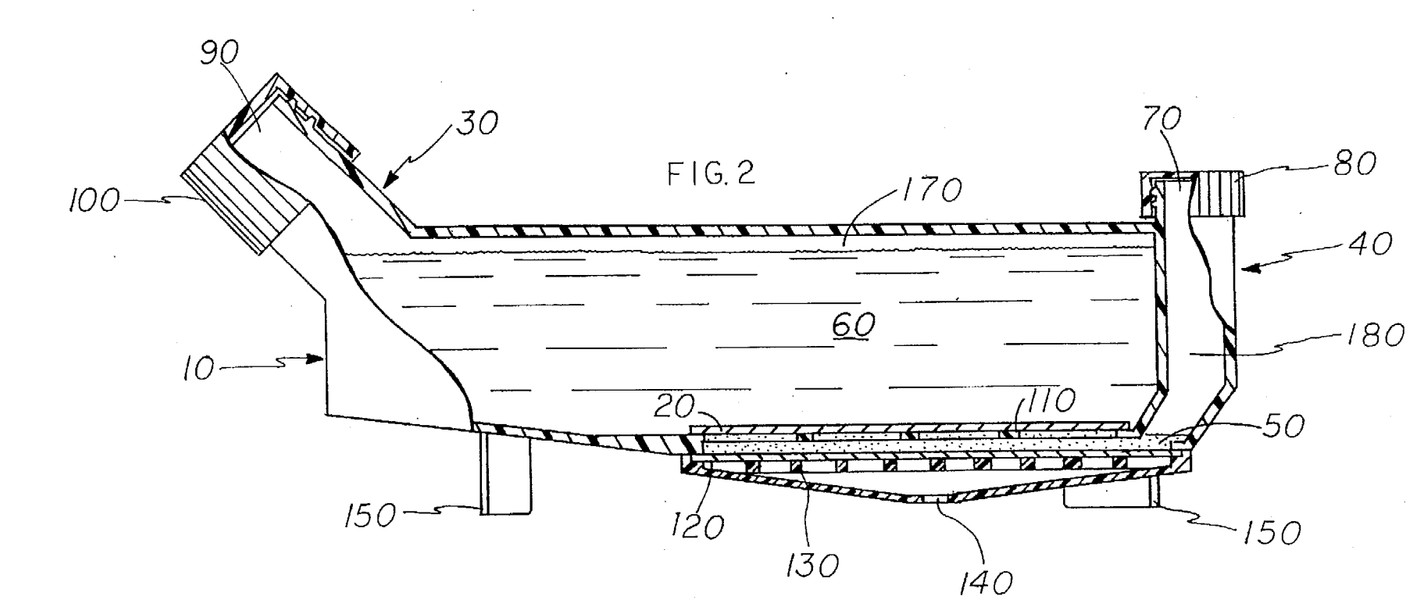
FIG. 2 is a cut away view taken through the center of the tissue culture flask of FIG. 1.

Referring now more specifically to the drawings, FIG. 1 shows an exploded view of a compartmentalized tissue culture flask 10. As shown in FIG. 2, a membrane 20 separates compartmentalized tissue culture flask 10 into a basal medium compartment 30 and a cell culture compartment 40. A culture medium 50 containing cells or tissue resides in cell culture compartment 40. A basal medium 60 resides in basal medium compartment 30. Access to cell culture compartment 40 is provided by a cell culture compartment access port 70 which is covered by a cell culture compartment access port cap 80. Access to basal medium compartment 30 is provided by a basal medium access port 90 which is covered by a basal medium access port cap 100. A membrane support 110 stabilizes membrane 20. A gas permeable film 120 resides on top of a gas film support 130 which is adapted to allow gas to contact the vast majority of the surface of gas permeable film 120 by way of a gas access opening 140. Feet 150 lift gas film support 130 above the surface on which compartmentalized tissue culture flask 10 resides.

In operation, culture medium 50 containing cells or tissue of interest is introduced into cell culture compartment 40 through cell culture compartment access port 70 until it makes complete contact with the underside of membrane 20. Basal medium 60 is introduced into basal medium compartment 30 through basal medium access port 90. Preferably, a basal medium head space 170 will be maintained between basal medium 60 and the top of basal medium compartment 30 and basal medium access port cap 100 will be slightly loosened. This allows ambient gas to influence the pH of basal medium 60. A basal medium access port cap of the type used in Falcon® tissue culture flasks (commercially available from Becton Dickinson Labware—Plymouth, England) may be used in cases where the cap should remain tightened due to contamination concerns.

Compartmentalized tissue culture flask 10 is designed to prevent pressurization as the temperature of the gas and liquid it contains rises when it is placed into an incubator. Cell culture access port cap 80 and basal medium access port cap 100 can be loosened to allow expanding gas to vent to the surrounding atmosphere. Culture medium 50 is free to expand into a culture medium head space 180 and basal medium 60 is free to expand into basal medium head space 170. In this manner pressure does not affect the flatness of gas permeable film 120, or liquid flux through either membrane 20 or gas permeable film 120.

Aside from fluid expansion, another phenomenon occurs as a result of the temperature increase. The gas carrying capacity of the liquid medium is lowered. Gas bubbles that are released by culture medium 50 can be moved to culture medium head space 180 by temporarily tilting compartmentalized tissue culture flask 10. This prevents the gas from becoming trapped against the bottom of membrane 20 and limiting dialysis.

Culture medium head space 180 is designed to counterbalance liquid transfer that may occur through membrane 50 due to hydrostatic pressure differential that results from head height differences in basal medium 60 and culture medium 50 at the time of set up. As liquid moves through membrane 20 into cell culture compartment 40, the level of culture medium in head space 180 rises. If cell culture compartment access port cap 80 is in the tightened position, the liquid will continue to rise in culture medium head space 180 until the hydrostatic pressure of culture medium 50 is balanced by the pressure of the displaced gas. If cell culture compartment access port cap 80 is in the loosened position, liquid will rise in culture medium head space 180 until it reaches a level where the diminished pressure differential across membrane 50 stops liquid transfer. In the preferred embodiment, the volume of culture medium 50 after flow has stopped will be no more than two times the volume of culture medium 50 at the onset of the culture.

Membrane 20 is a material selectively permeable to a class of molecules. Several types of material are acceptable including cellulose, polyacrylinitrile, polysulfone, polycarbonate, and polyacrilamide. For example, dialysis membranes retaining molecules and compounds with molecular weights greater than 15,000 are commonly used to culture murine hybridoma cells. By using a membrane with this characteristic, cells, growth factors, and secreted antibodies are retained in cell culture compartment 40. In other applications, it may be advantageous to allow larger molecules and compounds to pass freely between basal medium 60 and culture medium 50. For example, high density culture of lymphocytes may require a large quantity of growth stimulating factors to be present. These factors, such as interleukin 2, can be introduced into basal medium 60 and culture medium 50. By appropriately selecting the pore size of membrane 20, a large source of these factors can be made available to the lymphocytes.

Membrane support 110 stabilizes membrane 20. As basal medium 60 is added to basal medium compartment 30, the weight is transferred to membrane 20. Membrane support 110 keeps membrane 20 from sagging and displacing culture medium 50 into culture medium head space 180. Membrane support 110 makes minimal contact with membrane 50 so the surface area for dialysis is not substantially diminished. Membrane support 110 is designed such that it will allow gas bubbles to move freely to culture medium head space 180.

Membrane support 110 can be made of any biocompatible material. In the preferred embodiment it is clear plastic such as polystyrene or polycarbonate. If membrane 20 is a material cast onto a stiff mesh backing or precise control of the volume of culture medium 50 residing above gas permeable film 120 is not required, membrane support 110 is optional.

Figure 3:
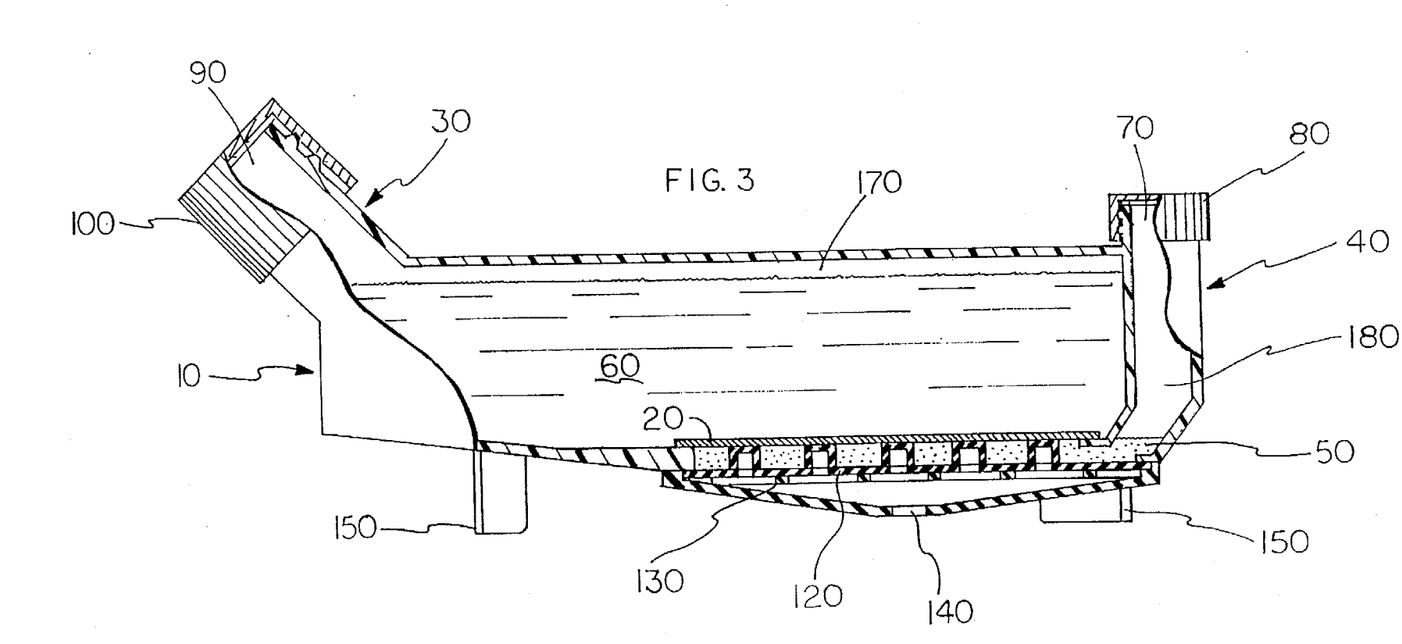
FIG. 3 is a cross-sectional view of a compartmentalized tissue culture flask showing an embodiment using gas permeable membrane, portions of which project into the cell culture compartment.

The embodiment of FIG. 3 shows a configuration where portions of gas permeable film 120 project into cell culture compartment 40 to provide support of membrane 20 without the need for membrane support 110. Silicone is a good choice for material as it can be readily molded to form an appropriate shape. Wall thickness can be minimized to allow additional gas transfer into cell culture compartment 40. In the case of silicone, average wall thickness should be kept below 0.015 inches, preferably about 0.004 to 0.012 inches.

Figure 4:
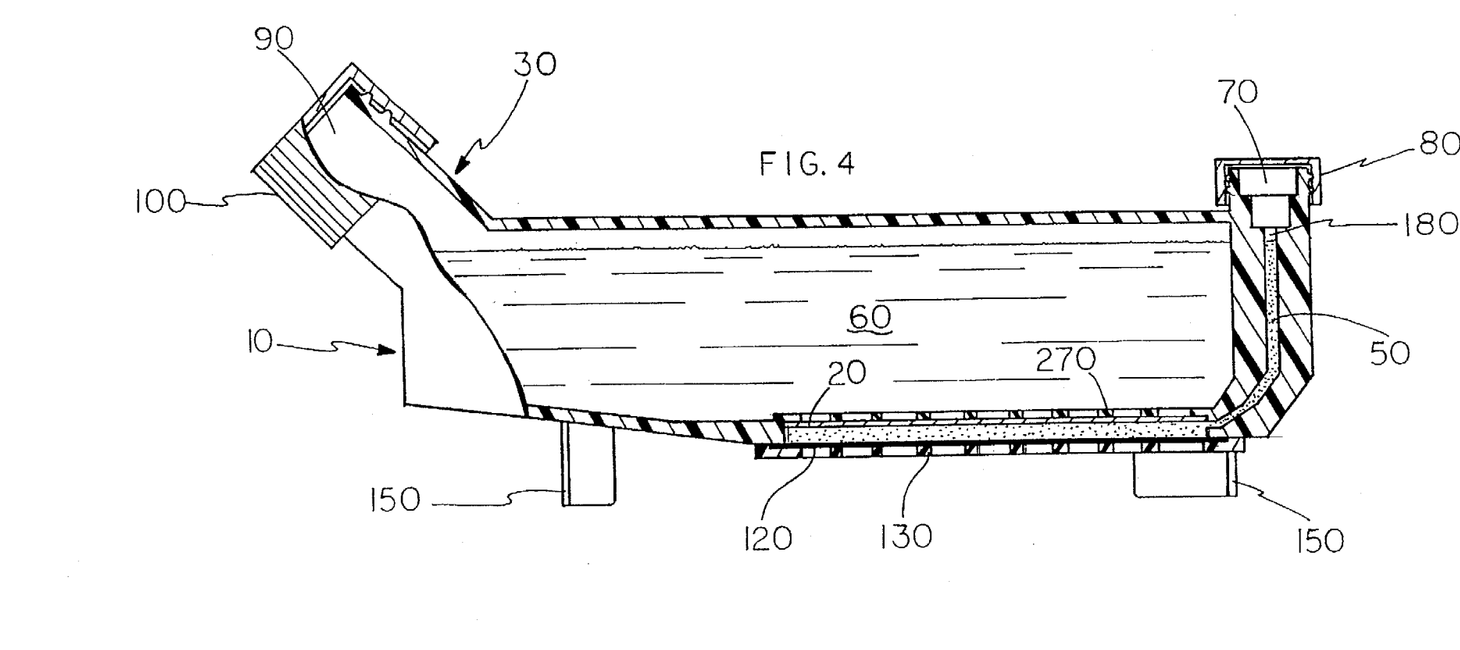
FIG. 4 is a cross-sectional view of a compartmentalized tissue culture flask showing an embodiment that balances hydrostatic pressure in two compartments.

The embodiment shown in FIG. 4 keeps membrane 20 from sagging and insures liquid maintains contact with the upper and lower surface of membrane 20 during operation. It is particularly useful for applications in which a high concentration of cells is desired. Membrane support 110 is not present and this allows a very small volume of culture medium 50 to be used as well as preventing obstacles to cell removal. This embodiment is also capable of functioning with various volumes of culture medium 50, as liquid contact with membrane 20 is always assured.

In operation, membrane 20 is pressed onto the surface of gas permeable film 120 by the weight of basal medium 60. Putting the membrane in this position can also be achieved by generating a vacuum on cell culture compartment 40. A predetermined volume of culture medium 50 containing the desired culture is then introduced into cell culture compartment 40 by way of cell culture compartment access port 70. When basal medium access port cap 100 and cell culture compartment access port cap 80 are in the vented position, culture medium 50 will come to rest within culture medium head space 180 at a level that counterbalances the hydrostatic pressure of basal medium 60.

In the preferred embodiment, the volume of culture medium 50 residing in culture medium head space 180 will be a small fraction of the volume of culture medium 50 residing between membrane 20 and gas permeable film 120. It is possible for water from basal medium 50 to move into cell culture compartment 40 if severe osmotic gradients develop across membrane 20. If this condition begins to occur, cell culture compartment access port cap 80 should be placed in the tightened position. This will prevent liquid from rising in culture medium head space 180.

Introducing culture medium 50 into cell culture compartment 40 will require enough pressure to overcome the hydrostatic pressure of basal medium 60. This can be accomplished by configuring cell culture compartment assess port 70 to accept a pipette, syringe, or some other culture medium container such as a bag or bottle. Culture medium 50 can be removed in the same manner.

This method of introducing culture medium 50 into cell culture compartment 40 and removing it therefrom can be utilized in all of the embodiments described herein. In most embodiments using membrane support 110, it will be necessary to provide a vent to allow air access to and from cell culture compartment 40. The vent is required to allow gas to be displaced when culture medium 50 is introduced into culture compartment 40. The vent also allows gas to displace culture medium 50 when it is removed from cell culture compartment 40. Cell culture compartment access port 70 is designed to allow gas to move in and out while culture medium 50 is added and removed. Thus, cell culture compartment 40 is effectively vented.

The embodiment of FIG. 4 does not require a vent. When membrane 20 is pressed against gas permeable film 120, air is displaced from cell culture compartment 40 prior to introducing culture medium 50. When culture medium 50 is removed, membrane 20 is simply lowered. Thus, there is never the need for gas and liquid to move to and from cell culture compartment 40 simultaneously.

When the embodiment shown in FIG. 4 is used for high density culture, the average distance between membrane 20 and gas permeable film 120 should be less than 5 millimeters, preferably about 1 mm to 2 mm.

The embodiment of FIG. 4 can also be used to prevent evaporation of culture medium 50 from allowing membrane 20 to loose contact with culture medium 50. Membrane 20 is essentially floating on culture medium 50 and as culture medium 50 evaporates through gas permeable film 120, membrane 20 simply gets closer to gas permeable film 120. No dialysis limitation occurs as membrane 20 is always in contact with culture medium 50.

In cases where membrane 20 is comprised of a material such as cellulose that swells or becomes baggy when wet, it will be desirable to constrain membrane 20 with an upper membrane support 270. Upper membrane support 270 stops upward travel of membrane 20 as culture medium 50 enters cell culture compartment 40. Culture medium 50 presses membrane 20 against upper membrane support 270, smoothing wrinkles.

Wrinkles in membrane 20 lead to an uneven distribution of cells during inoculation. If membrane 20 were severly wrinkled, culture medium 50 would reside within the wrinkles. Then some areas above gas permeable film 120 would have more culture medium 50 residing above it than others. Cells in the inoculum are distributed equally throughout culture medium 50. Eventually, these cells settle onto gas permeable film 120. Area of gas permeable film 120 in which a larger volume of culture medium 50 resides above it will receive more cells. Therefore, the wrinkling of membrane 20 should be minimized.

Upper membrane support 270 can be any biocompatible material such as virgin grade polystyrene or polypropylene. Care should be given to insure that it does not limit dialysis. In the preferred embodiment, it should be about 70% to 90% open.

Gas permeable film 120 is a biocompatible material capable of allowing transfer of gas into and out of cell culture compartment 40. Gas permeable film 120 can be either liquid permeable or impermeable, hydrophobic or hydrophilic, porous or non porous. Thickness can range above or below 0.25 mm. The best choice depends on the specific application. As a general guideline, the gas permeability of a given membrane should be considered in addition to the interaction of the membrane with either cells or protein structures. Liquid impermeable films of equivalent thickness will establish various steady state oxygen tension at the cell/film interface. FEP Teflon, silicone, and silicone polycarbonate copolymers will establish higher oxygen tension than polyethylene, polycarbonate, polypropylene, polysulfone or polypropylene. In applications where protein denaturization, non-specific protein binding, cell membrane damage, or cell attachment is affected by the surface chemistry of the film, hydrophilic surfaces are more suitable. In applications where it is desirable to maintain the entire cell membrane in contact with water, hydrated gels may be most suitable The use of certain materials not normally associated with gas exchange can expand the options available for controlling oxygen tension at the cell/film interface. For example, non-porous cellulose acetate has a relatively low oxygen gas permeability on the order of $7.3 \times 10^{-9}$ $cm^3.cm/(sec.cm^2.atm)$. When cellulose acetate is made porous, it will increase oxygen permeability as it absorbs culture medium 50 with an oxygen permeability of $1.4 \times 10^{-6}$ $cm^3.cm/(sec.cm^2.atm)$. In this manner, varying oxygen tension can be achieved by controlling the amount of culture medium 50 present in gas permeable film 120. Thus, oxygen tension variations will result by varying either the pore size, porosity, or tortuosity of gas permeable film 120.

Gas film support 130 holds gas permeable film 120 in a substantially horizontal position and stabilizes gas permeable film 120 to prevent sagging. Care should be given to assure the flatness of gas permeable film is such that cells do not roll into or otherwise collect in low points. This is an undesirable event as the piling up of cells will create diffusional limitations and lead to cell death. On the other hand, care must also be taken to assure that gas exchange remains adequate. Thus, the optimal amount of contact gas film support 130 makes with gas permeable film 120 will depend on the stiffness and gas permeability of gas permeable film 120 as well as gas exchange and metabolic requirements of a particular cell culture application. It should be expected that most cell lines will become diffusionally limited at about ten to fifteen cell layers.

Gas film support 130 also acts to protect gas permeable film 120 from contamination or puncture. Minimal contact with gas permeable film 120 is made to allow the maximum possible surface area for gas transfer. Gas access opening 140 is located at the lowest point of gas film support 130 to allow condensation to exit gas film support 130. It is sized to allow adequate gas exchange of cell culture compartment 40 while minimizing evaporation. Gas film support 130 can be made of any structurally stable material, but in the preferred embodiment is an optically clear material such as polystyrene or polycarbonate to allow visual inspection of the culture in cases where gas permeable film 120 is optically clear. Feet 150 elevate compartmentalized tissue culture flask 10 such that gas film support 130 does not become scratched or visually impaired.

Another consideration with regard to material selection for gas permeable film 120 is the moisture vapor transmission rate. Culture medium 50 will evaporate at various rates pending the material selection of gas permeable film 120. Limiting the cross-sectional area of gas access opening 140 can reduce the rate of evaporation, although the rate of liquid loss will also be a function of the ambient humidity which is more difficult to control. The embodiment of FIG. 5 addresses this issue.

Figure 5:
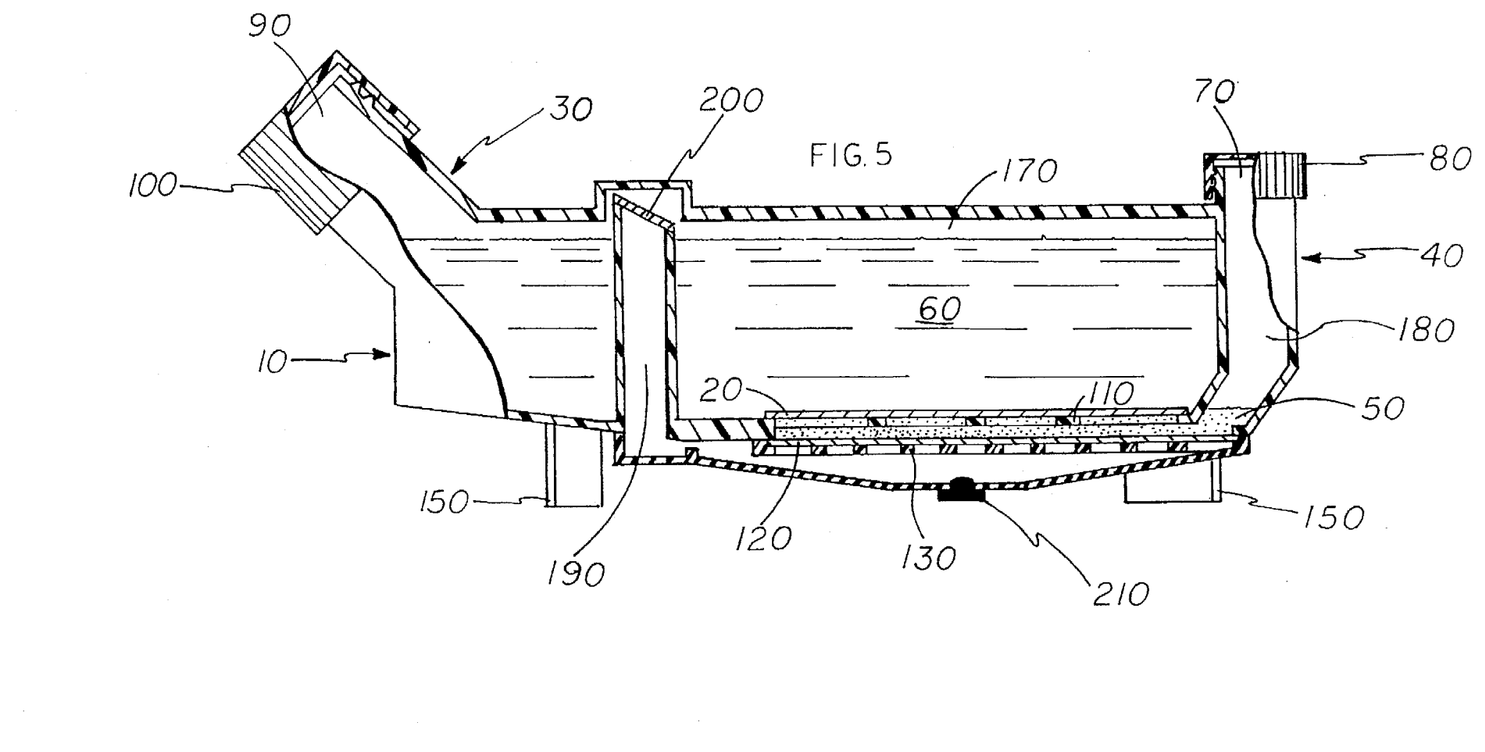
FIG. 5 is a cross-sectional view of a compartmentalized tissue culture flask showing an embodiment that controls evaporation.

The humidified gas of basal medium head space 170 is placed in communication with the underside of gas permeable film 120 by a gas access channel 190. A gas access channel cover 200 prevents basal medium 60 from entering gas access channel 190 and limiting gas transfer. Gas access channel cover 200 is a gas permeable, liquid impermeable film. To prevent condensation from accumulating upon gas access channel cover 200 and diminishing gas transfer, it is not in a horizontal position. Thus, condensation can return to basal medium 60 by gravitational force. Also, gas access channel 190 is capable of collecting condensation in a drain port 210.

Many other methods of placing basal medium head space 170 in communication with gas permeable film 120 are possible. Care should be given to prevent condensation or basal medium 60 from diminishing gas transfer.

Figure 6:
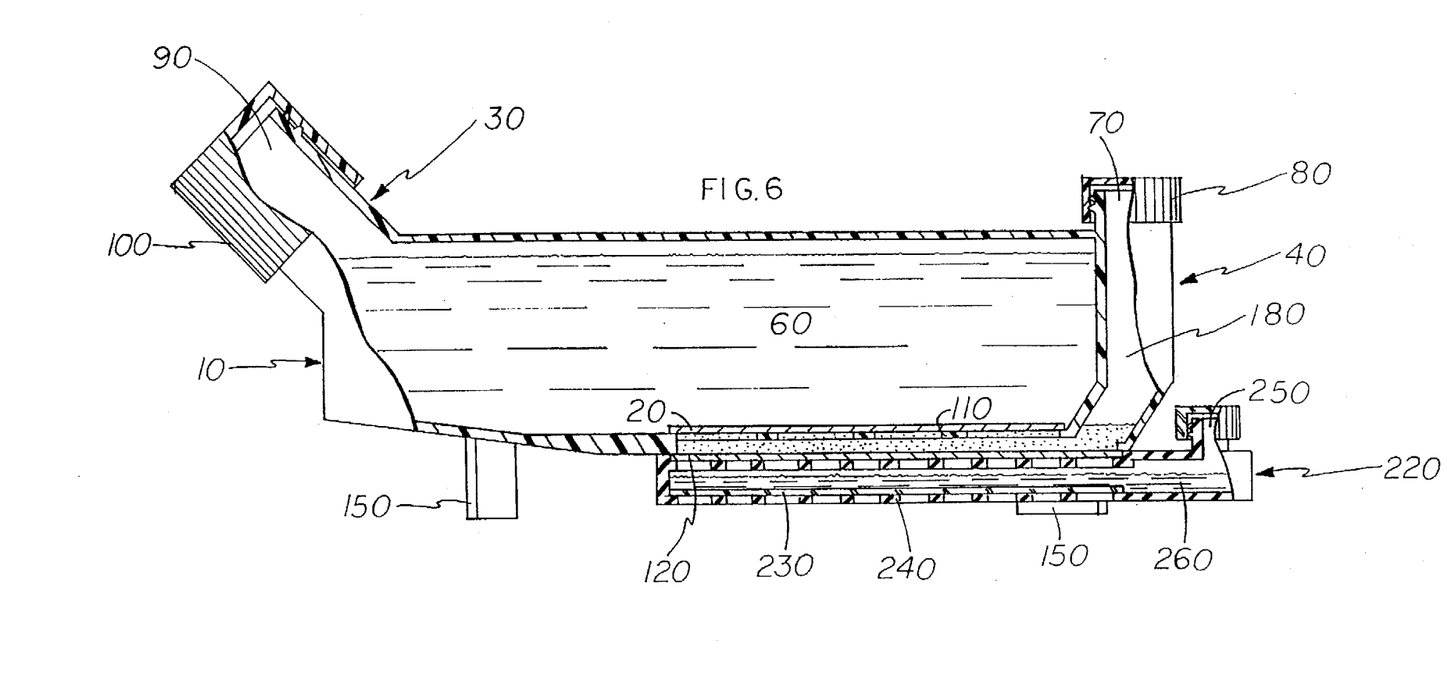
FIG. 6 is a cross-sectional view of compartmentalized tissue culture flask showing an embodiment that allows variable oxygen tension.

If the type of materials available for gas permeable film 120 do not provide the desired oxygen tension, the configuration shown in FIG. 6 can be utilized. A variable oxygen control compartment 220 is composed of a lower gas permeable film 230 supported in a horizontal position by an oxygen control compartment bottom 240. An oxygen control compartment access port 250 allows a liquid resistor 260 to be introduced into variable oxygen control compartment 220. The oxygen tension at the bottom of gas permeable film 120 can be carefully controlled by varying the height of liquid residing upon a lower gas permeable film 230 in accordance with Fick's Law. Lower gas permeable film 230 can be any highly gas permeable film or sheet. In the preferred embodiment, it is liquid impermeable and has a relatively low moisture vapor transmission rate. Oxygen control compartment bottom 240 allows the vast majority of lower gas permeable film 230 to be in communication with the ambient environment. A hermetic seal exists between lower gas permeable film 230 and oxygen control compartment bottom 240. This seal can be made by welding, adhesives, or any other suitable method. The distance between the top of lower gas permeable film 230 and the bottom of gas permeable film 120 will preferably be about 5 to 20 mm.

To minimize evaporation of liquid residing in variable oxygen control compartment 220, the underside of lower gas permeable film 230 can be placed in gaseous communication with basal medium head space 170 as previously described.

Although there is no restriction on either the shape or size of cell culture compartment 40, the advantageous distance between gas permeable film 120 and membrane 20 is about 1 to 4 millimeters to obtain a high concentration of cells and cell secreted products. When gas permeable film 120 is substantially flat and horizontal, up to 30×10$^6$ cells per square centimeter of surface area can be expected to remain viable. These cells can pile up to a height of about 300 micrometers. Thus, membrane 20 is in no danger of contacting cells and becoming clogged when it resides at least 1 mm from gas permeable film 120.

In order to minimize the frequency of basal medium 60 exchanges, the volume of basal medium 30 is sized relative to the surface area of gas permeable film 120. For suspension cells that reside in static culture at one million cells per milliliter, about 5 to 10 ml of basal medium 60 are required for every 1 cm$^2$ of gas permeable film 120. When culturing anchorage dependent cells growing in monolayer, advantageously the volume of basal medium 60 exceeds the surface area of gas permeable film 120 by at least a factor of two.

The housing of compartmentalized culture flask 10 can be any biocompatible material. In the preferred embodiment, the housing will provide optical clarity so the medium can be visually monitored for determining the pH of the medium or detecting possible microbial contamination. Polystyrene is a favored selection. Construction of compartmentalized tissue culture flask 10 can be by ultrasonic welding, mechanical fasteners, solvent bonding or any other method which provides leak proof integrity. Gas permeable film 120 and membrane 20 can be sealed by o-rings, gaskets, welding, adhesives, or any other method which provides leak proof integrity. In the preferred embodiment, all materials used in the compartmentalized tissue culture flask 10 should be compatible with gamma sterilization.

Those skilled in the art will appreciate that numerous modifications can be made thereof without departing from the spirit. Therefore, it is not intended to limit the breadth of the invention to the embodiments illustrated and described. Rather, the scope of the invention is to be determined by the appended claims and their equivalents.

What is claimed is:

1. A cell culture device consisting essentially of a container having
   a) a cell culture compartment defined by a lower gas permeable film and an upper sheet selectively permeable to compounds of less than a particular size and adapted to allow a culture medium to reside between said upper sheet and said lower gas permeable film;
   b) a basal medium compartment above said upper sheet and adapted to allow a basal medium to reside upon said upper sheet;
   c) only one access port to said cell culture compartment;
   d) an access port to said basal medium compartment; and
   e) a gas film support below and in partial contact with said gas permeable film whereby the majority of said gas permeable film is held in a substantially horizontal position such that suspension cells can distribute across a horizontal portion of said gas permeable film and gas transfer into and out of said cell culture compartment is not substantially impaired.

2. A device according to claim 1 wherein the surface area of said upper sheet is at least one quarter of the surface area of said lower gas permeable film.

3. A device according to claim 1 wherein the average distance between the substantially horizontal portion of said lower gas permeable film and said upper sheet is less than 15 millimeters.

4. A device according to claim 1 wherein said gas film support is adapted such that the smallest cross-sectional area of said gas film support open to gaseous communication with the ambient environment is less than the total surface area of said lower gas permeable film in contact with gas.

5. A device according to claim 1 wherein an upper sheet support resides below and in partial contact with said upper sheet.

6. A device according to claim 1 wherein the entrance of said access port to said basal medium compartment is positioned higher than the top of said basal medium compartment.

7. A cell culture device comprising a container having
   a) a cell culture compartment comprised of a lower gas permeable film and an upper sheet selectively permeable to compounds of less than a particular size and by appropriate means adapted to allow a culture medium to reside between said upper sheet and said lower gas permeable film;
   b) a basal medium compartment above said sheet and adapted to allow a basal medium to reside upon said upper sheet and a gas to reside above and in contact with said basal medium;
   c) an access port to said cell culture compartment;
   d) an access port to said basal medium compartment;
   e) a gas film support below and in partial contact with said gas permeable film whereby the majority of said gas permeable film is held in a substantially horizontal position such that suspension cells can distribute across a horizontal portion of said gas permeable film and gas transfer into and out of said cell culture compartment is not substantially impaired; and
   f) a gas exchange compartment adapted by appropriate means to provide gaseous communication between said gas of said basal medium compartment and the underside of said gas permeable film.

8. A device according to claim 7 wherein said lower gas permeable film includes sections which project into said cell culture compartment.

9. A device according to claim 7 wherein said gas exchange compartment is adapted to prevent said basal medium from entering said gas exchange compartment.

10. A device according to claim 7 wherein said gas exchange compartment has an access port whereby condensation can be removed and gas other than that of said basal medium compartment can communicate with the underside of said gas film.

11. A cell culture device comprising a container having
   a) a cell culture compartment defined by a first gas permeable film and an upper sheet selectively permeable to compounds of less than a particular size and separated by appropriate means to allow a culture medium to reside between said upper sheet and said first gas permeable film;
   b) a basal medium compartment above said upper sheet and adapted by appropriate means to allow a basal medium to reside in contact with said upper sheet;
   c) an access port to said cell culture compartment;
   d) an access port to said basal medium compartment;
   e) a gas film support below and in partial contact with said first gas permeable film whereby the majority of said gas permeable film is held in a substantially horizontal position such that suspension cells can distribute across a horizontal portion of said gas permeable film and gas transfer into and out of said cell culture compartment is not substantially impaired;
   f) a second gas permeable film disposed in a horizontal position below said first gas permeable film;
   g) one separating means between said first gas permeable film and said second gas permeable film to form an oxygen tension control compartment adapted to contain fluid; and
   h) an access port to said oxygen tension control compartment whereby liquid can be added or removed to control the rate of gas transport.

12. A device according to claim 11 wherein said first gas permeable film includes sections which project into said cell culture compartment.

13. A method of culturing cells comprising the steps of:
   a) forming a cell culture compartment, said cell culture compartment comprised of a lower gas permeable film and an upper sheet permeable to a selected class of compounds;
   b) forming a gas film support, said gas film support being disposed below said gas permeable film and adapted to hold at least a portion of said gas permeable film in a substantially horizontal position while allowing gas to contact the underside of said gas permeable film;
   c) placing a basal medium in a second compartment above said upper sheet said basal medium in contact with said upper sheet;
   d) placing the cells and a cell culture medium in said cell culture compartment said cell culture medium in contact with said upper sheet;
   e) maintaining cells at a selected temperature; and
   f) allowing gas exchange through said lower gas permeable film without perfusion whereby cells are allowed to proliferate in high density upon the entire surface of said lower gas permeable film.

14. A method of culturing cells comprising the steps of:
   a) forming a cell culture compartment, said cell culture compartment being comprised of a gas permeable film disposed below an upper sheet permeable to a selected class of compounds;
   b) forming a gas film support, said gas film support being disposed below said gas permeable film and adapted to hold at least a portion of said gas permeable film in a substantially horizontal position while allowing gas to contact the underside of said gas permeable film;
   c) placing a basal medium in a basal medium compartment above said upper sheet said basal medium in contact with said upper sheet;
   d) placing the cells and a cell culture medium in said cell culture compartment said cell culture medium in contact with said upper sheet;
   e) maintaining cells at a selected temperature; and
   f) allowing gas exchange through said lower gas permeable film whereby cells are allowed to proliferate upon the entire surface of said lower gas permeable film; and
   g) structuring said film support such that the smallest cross-sectional area of said gas film support open to gaseous communication with the ambient environment is less than the total surface area of said gas permeable film in contact with gas, thereby reducing moisture vapor transmission.

15. The method of claim 14 wherein the average distance between said upper sheet and the substantially horizontal portion of said lower gas permeable film does not exceed 15 millimeters.

16. A method of culturing cells comprising the steps:
   a) forming a cell culture compartment, said cell culture compartment comprised of a lower gas permeable, liquid permeable film and an upper sheet permeable to a selected class of compounds;
   b) placing a basal medium in a second compartment above said upper sheet, said basal medium in contact with said upper sheet;
   c) placing the cells and a cell culture medium in said cell culture compartment, said cell culture medium in contact with said upper sheet;
   d) maintaining cells at an appropriate temperature; and
   e) allowing gas to reside below said lower gas permeable, liquid permeable film.

17. A method according to claim 16 wherein said lower gas permeable, liquid permeable film including sections which project into said cell culture compartment.

18. A method of culturing cells comprising the steps:
   a) forming a cell culture compartment, said cell culture compartment comprised of a lower first gas permeable film and an upper sheet permeable to a selected class of compounds;
   b) placing said cell culture compartment upon an oxygen control compartment comprised of an upper support mesh and a bottom second gas permeable film, said support mesh maintaining said lower first gas permeable film in a substantially horizontal position;
   c) placing a basal medium in a basal medium compartment above said upper sheet, said basal medium in contact with said upper sheet;
   d) placing the cells and a cell culture medium in said cell culture compartment, said cell culture medium in contact with said upper sheet;
   e) placing a selected volume of a liquid into said oxygen control compartment;

f) maintaining cells at an appropriate temperature;

g) allowing oxygen and carbon dioxide to diffuse through said lower gas permeable film by way of said liquid and said bottom second gas permeable film of said oxygen control compartment whereby cells are allowed to proliferate upon the entire surface of said lower first gas permeable film, evaporation of said cell culture medium is limited, and oxygen tension within said cell culture compartment can be varied by adding or removing said liquid from said oxygen control compartment.

19. A method according to claim 18 wherein said lower first gas permeable film includes sections which project into said cell culture compartment.

20. A cell culture device comprised of a container having:

a) a cell culture compartment defined by a lower gas permeable film including sections which project into said cell culture compartment and by an upper sheet selectively permeable to compounds and adapted to allow a culture medium to reside between said upper sheet and said lower gas permeable film;

b) a basal medium compartment above said upper sheet and adapted to allow a basal medium to reside upon said upper sheet;

c) an access port to said cell culture compartment;

d) an access port to said basal medium compartment; and e) a gas film support below and in partial contact with said gas permeable film whereby the majority of said gas permeable film is held in a substantially horizontal position such that suspension cells can distribute across a horizontal portion of said gas permeable film and gas transfer into and out of said cell culture compartment is not substantially impaired.

21. A method of culturing cells comprising the steps of:

a) forming a cell culture compartment comprised of a lower gas permeable film including sections which project into said cell culture compartment and of an upper sheet permeable to a selected class of compounds;

b) maintaining said lower gas permeable film in a substantially horizontal position;

c) placing a basal medium in a second compartment above said upper sheet said basal medium in contact with said upper sheet;

d) placing the cells and a cell culture medium in said cell culture compartment said cell culture medium in contact with said upper sheet;

e) maintaining cells at a selected temperature; and f) allowing gas exchange through said lower gas permeable film without perfusion whereby cells are allowed to proliferate in high density upon the entire surface of said lower gas permeable film.

22. A method of culturing cells comprising the steps of:

a) forming a cell culture compartment, said cell culture compartment being comprised of a lower gas permeable, liquid permeable film and an upper sheet permeable to a selected class of compounds, said lower gas permeable, liquid permeable film including sections which project into said cell culture compartment;

b) placing a basal medium in a second compartment above said upper sheet said basal medium in contact with said upper sheet;

c) placing the cells and a cell culture medium in said cell culture compartment said cell culture medium in contact with said upper sheet;

d) maintaining cells at an appropriate temperature; and e) allowing gas exchange through said lower gas permeable, liquid permeable film.

23. A method of culturing cells comprising the steps:

a) forming a cell culture compartment, said cell culture compartment being comprised of a lower gas permeable film and an upper sheet permeable to a selected class of compounds;

b) forming a basal medium compartment, said basal medium compartment being adapted to hold a basal medium in contact with said upper sheet of said cell culture compartment;

c) placing said basal medium into said basal medium compartment;

d) forming an access port to said cell culture compartment, the entrance to said access port residing at a height greater than or equal to said basal medium;

e) maintaining said lower gas permeable film in a substantially horizontal position;

f) placing the cells and a cell culture medium in said cell culture compartment with said cell culture medium in contact with the underside of said upper sheet;

g) allowing the liquid level in said culture compartment to rise into said access port of said cell culture compartment to counter balance the hydrostatic pressure of said basal medium;

h) maintaining cells at a selected temperature; and i) allowing gas exchange through said lower gas permeable film whereby cells are allowed to proliferate upon the entire surface of said lower gas permeable film.

24. A method of culturing cells comprising the steps of:

a) forming a cell culture compartment, said cell culture compartment being comprised of a lower gas permeable film and an upper sheet permeable to a selected class of compounds; said lower gas permeable film including sections which project into said cell culture compartment;

b) forming a basal medium compartment, said basal medium compartment adapted to hold a basal medium in contact with said upper sheet of said cell culture compartment;

c) placing said basal medium into said basal medium compartment;

d) forming an access port to said cell culture compartment the entrance to said access port residing at a height greater than or equal to said basal medium;

e) maintaining said lower gas permeable film in a substantially horizontal position;

f) placing the cells and a cell culture medium in said cell culture compartment said cell culture medium in contact with the underside of said upper sheet;

g) allowing the liquid level in said cell culture compartment to rise into said access port of said cell compartment to counter balance the hydrostatic pressure of said basal medium;

h) maintaining cells at a selected temperature; and i) allowing gas exchange through said lower gas permeable film whereby cells are allowed to proliferate upon the entire surface of said lower gas permeable film.

* * * * *